United States Patent [19]

Sumikama et al.

[11] 4,126,393
[45] Nov. 21, 1978

[54] HIGH-SENSITIVITY DIFFERENTIAL REFRACTOMETER

[75] Inventors: Sadao Sumikama; Shigeru Nakamura, both of Yokohama; Kozo Shirato, Ohmiya; Kazuo Hiraizumi, Funabashi; Nobuo Takasu, Kawaguchi; Mitsuru Taguchi, Yokohama; Tsuyoshi Yamada, Yokohama; Susumu Ishiguro, Yokohama, all of Japan

[73] Assignees: Showa Denko K. K; Erma Optical Works, Ltd., both of Tokyo, Japan

[21] Appl. No.: 772,212

[22] Filed: Feb. 25, 1977

[30] Foreign Application Priority Data

Mar. 2, 1976 [JP] Japan .................................. 51/21812
Mar. 2, 1976 [JP] Japan .................................. 51/23994
Jul. 7, 1976 [JP] Japan .................................. 51/89395

[51] Int. Cl.$^2$ ............................................. G01N 21/46
[52] U.S. Cl. .................................... 356/130; 350/285
[58] Field of Search ............... 356/128, 130, 131, 132; 350/285

[56] References Cited

U.S. PATENT DOCUMENTS

| 2,427,996 | 9/1947 | Seaman | 356/130 |
| 3,539,263 | 11/1970 | Waters | 356/131 |
| 3,619,068 | 11/1971 | Broerman | 356/130 |

FOREIGN PATENT DOCUMENTS

695,833 8/1953 United Kingdom ..................... 356/131

Primary Examiner—John K. Corbin
Assistant Examiner—R. A. Rosenberger
Attorney, Agent, or Firm—Oblon, Fisher, Spivak, McClelland & Maier

[57] ABSTRACT

Disclosed herein is a high-sensitivity differential refractometer which is characterized by having a light source disposed outside a housing, a reflecting mirror attached at the end portion thereof to a reflecting mirror-supporting plate connected with the end of a movable plate, said movable plate being so constructed as to rotate around a vertical axis and permit free change of the angle formed between said reflecting mirror-supporting plate and the movable plate, a twisting member disposed inside a lead-in tube and said lead-in tube fastened to a removable case and built in a metallic block inside the housing.

6 Claims, 16 Drawing Figures

HIGH-SENSITIVITY DIFFERENTIAL REFRACTOMETER

BACKGROUND OF THE INVENTION

This invention relates to a high-sensitivity differential refractometer of improved measuring precision for use in liquid chromatography.

Every substance has its own index of refraction. The high-sensitivity differential refractometer is an instrument for measuring the index of refraction of a solution subjected to measurement by means of a junction-prism type cell containing in one end section thereof a solvent serving as the reference specimen and in the other end section thereof a test specimen on said solution, with the measurement being made by utilizing the change in the index of refraction of light which is caused when a light is passed through said cell.

The high-sensitivity differential refractometer (hereinafter referred to as "refractometer") permits even a very slight change of concentration in any solution to be measured continuously and with high accuracy in terms of the difference in refractive index between a test specimen of said solution and a solvent serving as the reference specimen. Owing to the high sensitivity of the measurement, this instrument has found extensive adoption as a detector in the liquid chromatography.

Generally, the refractometer has as its principal components, a cell adapted to pass the solvent and the test specimen into the interior of the housing so as to cause a refraction of light corresponding to the difference between the indices of refraction of the two liquids, a light-source lens adapted to pass the light through the cell, a mirror or some other similar article serving to reflect the incident light, an optical base for holding said mirror in position and an element for detecting the reflected light. The index of refraction of a solution is very sensitively affected by the temperature of said solution. In the detection of a very minute change in the index of refraction of the order of $1 \times 10^{-7}$, for example, a change of temperature as slight as 0.001° C. can cause a large enough drift of the base line to degrade the accuracy of measurement. This means that during actual measurement the temperature change in the cell interior and the difference of temperature between the liquid held inside the cell and the solvent must be minimized as much as possible.

Given below are the three major causes for temperature change or ununiform temperature distribution in the cell interior.

a. Local heating by light-source lamp.
b. Thermal effect exerted externally.
c. Temperature difference between the test specimen passed into the cell interior and the solvent and consequent change of temperature.

The measure conventionally adopted to cope with the cause "a" is to provide the lamp with a cooling device or to select a lamp of the kind designed to suppress heavy generation of heat. The former measure has the disadvantage that the addition of said extra device complicates the refractometer as a whole and adds to the price thereof. The latter measure entails a degradation in the accuracy of the refractometer.

The conventional measure adopted to cope with the cause of "b" is to wrap the optical base in a heat insulating material.

The measure taken to cope with the cause of "c" is to keep the temperature of the specimen as close to the temperature of the cell as permissible by either causing the lead-in pipe forming a passage between the exterior and the interior of the cell to be buried in a metallic block or powder having a great heat capacity or passing the pipe through a heat-exchange unit. This pipe serves the purpose of forwarding to the cell the separated liquid which is discharged from the liquid chromatograph. To prevent the pipe from permitting undesirable mixing of solution, the length (inner volume) of the pipe must be reduced to the tolerable minimum. The pipe to the cell is generally made of a highly anticorrosive stainless steel pipe having an inside diameter of not more than 0.5 mm. The flow rate of the liquid within this pipe is in the range of from 4 to 10 cm per second. And the pipe has a limited length. With the pipe of such a description, it is difficult to provide ample exchange of heat. When the refractometer is operated to make the measurement, the optical axis or the position of the reflecting mirror must be adjusted so that the light projected from the light source, passed through the array of lenses and reflected by the reflecting mirror will impinge correctly upon the desired position on the detection unit.

In the conventional refractometer, the reflecting mirror is attached in position in the manner described below.

Figure 1:
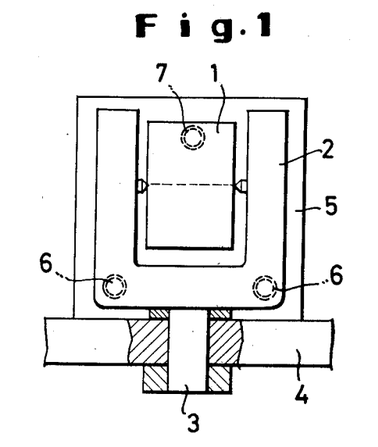
FIG. 1 is a front view of a conventional construction for the attachment of a reflecting mirror designed to provide adjustment of the optical axis.
Figure 2:
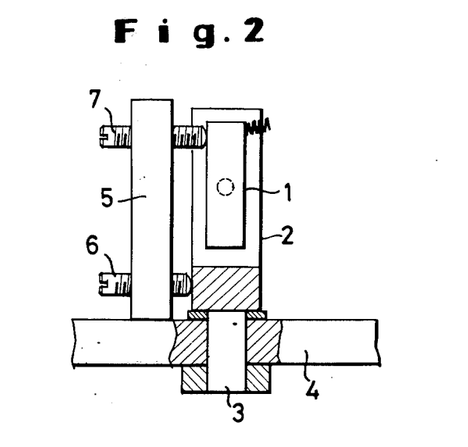
FIG. 2 is a side view of the construction of FIG. 1.

FIG. 1 is a front view of the structure for fixing the reflecting mirror in position and FIG. 2 is a side view of said structure.

In the drawings, a reflecting mirror 1 is supported by a frame 2. This reflecting mirror is adapted so as to be freely rotated around the horizontal axis (indicated by the dotted line in the drawing) thereof. Said frame 2 is supported by a supporting shaft 3 and the supporting shaft 3 is supported in position by a shaft receiving member 4. To the shaft-receiving member is fastened a stationary wall 5. The stationary wall 5 is provided with threaded pins 6, 6 and 7.

In this construction, required adjustment of the position of the reflecting mirror is accomplished by rotating the reflecting mirror around the horizontal axis by the movement of the threaded pins 7 and by rotating it clockwise or counterclockwise about its vertical axis by the movement of the threaded pins 6, 6.

Since the threaded pins 6, 6 disposed at laterally opposite positions give a push in one direction to the frame 2 in this construction, a resilient strain is imparted to the frame 2, with the inevitable result that any attempt to shift the optical axis right or left in the horizontal direction will also affect the condition of the optical axis in its vertical direction. Since the threaded pin 7 protrudes from the stationary wall 5, the point at which the threaded pin 7 comes into contact with the rear side of the reflecting mirror 1 is varied by the rotary movement of the frame 2. Consequently, the horizontal adjustment of the optical axis upsets the vertical adjustment thereof. The exact reverse of this relationship also occurs, though to a very slight extent.

For this reason, the adjustment of the optical axis in refractometry has heretofore been time-consuming and called for skill.

One object of the present invention is to provide a high-sensitivity differential refractometer which permits the measurement of the refractive index of a solution with extremely high accuracy substantially free from the influence of the temperature of said solution.

Another object of the present invention is to provide a high-sensitivity differential refractometer of a construction such that the adjustment of the position of the reflecting mirror is accomplished with extreme ease.

SUMMARY OF THE INVENTION

To attain the objects described above, the high-sensitivity differential refractometer according to the present invention has, as the principal components thereof, a housing, a light source, light-refracting means comprising a cell, lenses and a reflecting mirror and disposed inside said housing, light-sensing means, a conduit for introducing a sample liquid into the cell and a liquid-chromatographic column. Additional features embraced in the present invention are that the light source is disposed outside the housing for the purpose of keeping the test specimen of solution and the solvent free from the effect of temperature while in transit through the cell interior that a twisted member is inserted inside the conduit for the introduction of test specimen into the cell for the purpose of increasing the surface area available for heat transfer and uniformizing temperature distribution within the conduit and that the conduit for the introduction of test specimen may be disposed inside a case which is removably attached to the interior of the housing.

The present invention further provides a high-sensitivity differential refractometer of a construction such that the means for adjusting the path of light emitted from the light source passed through the cell, reflected by the reflecting mirror and received in the reflected-light detection unit, i.e., for adjusting the optical axis has, as it principal components, a reflecting mirror-supporting member supporting the reflecting mirror in position and a movable plate adapted to be rotated around the vertical axis thereof and connected at the lower end thereof to said reflecting mirror-supporting member, said reflecting mirror-supporting member being provided with means adapted to permit said reflecting mirror-supporting to swing about the portion there of connected to said movable plate thus varying the angle formed between the reflecting mirror-supporting member and the movable plate.

DETAILED DESCRIPTION OF THE INVENTION:

This invention will be described with reference to the accompanying drawings.

Figure 3:
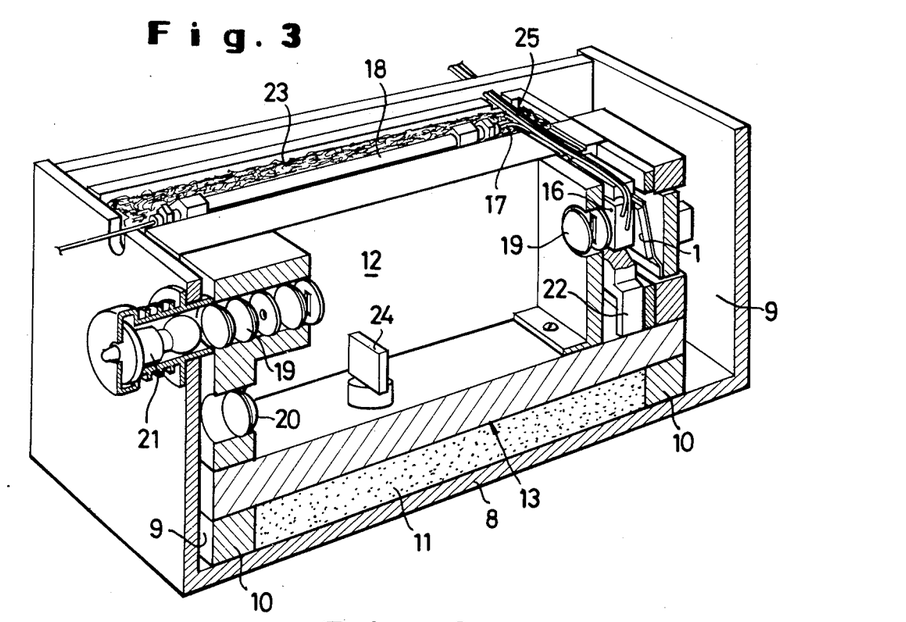
FIG. 3 is a perspective view of one preferred embodiment of the refractometer according to this invention.
Figure 4:
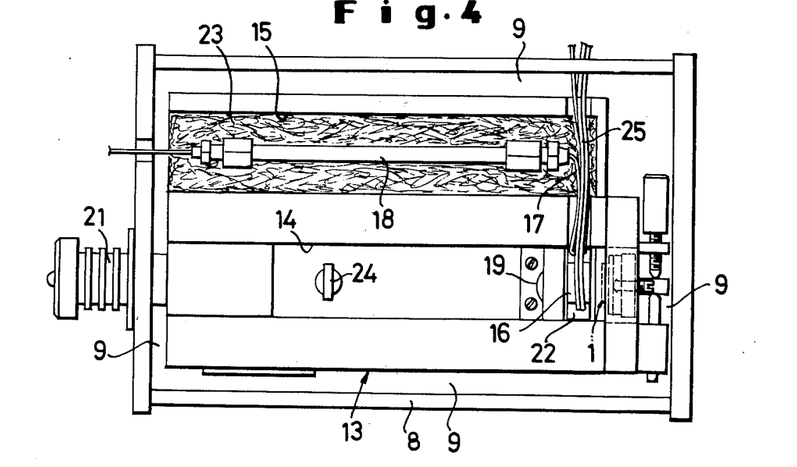
FIG. 4 is a plan view of the refractometer of FIG. 3.

FIG. 3 is a perspective view of one preferred embodiment of this invention, having the top side and the frontal side wall removed to expose the interior. FIG. 4 is a plan view of the embodiment of FIG. 3, with the top side removed. In the drawings, an outer shell 8 and air layers 9 and insulating materials 10, 11 formed inside said outer shell 8 are arranged so as to keep the interior of the housing from being affected by the heat outside the housing. Denoted by 12 is a central portion which is enclosed with said air layers and insulating materials. This central portion, to ensure uniform distribution of temperature therein, has the following structure. By 13 is denoted an optical base made of a metal plate having a large thickness. On this optical base 13, a groove 14 for a light path and a groove 15 for a liquid chromatographic column are formed parallelly with each other. There are also disposed a cell 16, a conduit 17, a liquid chromatographic column 18 and lenses 19, a reflecting mirror 1 and a photoelectric sensor 20 as component parts of the optical system. Further, 21 denotes a light source which is fixed outside the outer shell 8 and 22 denotes a cell supporting base which permits the cell 16 to be attached in an insulated state to the optical base 13. The space intervening between the groove 15 and the column 18 on the optical base 13 is filled up with a good heat-conducting material such as, for example, copper wool 23.

The light source 21 is held inside a light-source tube fastened to the outside of the outer shell 8. The light projected into the interior of the housing through a hole bored in the outer shell passes through the array of lenses 19 and reaches the cell 16. The light is refracted by the cell 16, then reflected by the reflecting mirror 1 and sent back to the cell 16. The light which is again refracted by the cell 16 is now passed through the balance glass 24 and received in the photoelectric sensor 20. This sensor 20 possesses a pair of photocells. As is well known in the art, the change in the refraction of light causes a corresponding change in the potential difference between the two photocells, registering the change in concentration of the solution under test. The cell, lenses and reflecting mirror jointly constitute the light-reflecting means and the photoelectric sensor constitutes the light-sensing means. Generally, the liquid chromatographic column 18 exists independently of the refractometer. In the preferred embodiment illustrated in FIG. 3 and FIG. 4, the column 18 in its entirety is held inside the groove 15 of the optical base 13 and is kept at the same temperature as the optical base 13 by the medium of the copper wool 23 which is a good conductor of heat. This effect of temperature equalization is obtained even when only the liquid outlet side of the column is held inside the groove and wrapped in the copper wool. Since the linear velocity of liquid inside the column 18 is from 1/10 to 1/100 of that inside the conduit 17, the effect of temperature equalization by this method is decidedly high compared with the conventional method whereby the liquid forwarded from the externally disposed chromatographic column to the refractometer undergoes exchange of heat before the liquid in transit reaches the conduit immediately preceding the refractometer. Since the flow of the solvent through the conduit 25 ceases at the time that the solvent fills the cell to capacity, the temperature of the solvent is readily equalized with that of the constant-temperature portion. This means that the solvent requires no special device for exchange of heat. The solvent may be forwarded through the groovve 15 to the cell 16 so that it will reach the constant temperature quickly.

Now the improvement with respect to the light source will be described. The light source is an indispensable element for the differential refractometer. For the refractometer to enjoy high sensitivity and precision, the light source is required to emit a light of high intensity. For the sensitivity and precision to be maintained at high levels, it is necessary that the temperature of the cell and that of the liquid should be held constant. Elimination of the possible effects of the light source upon these temperatures may be accomplished by keeping an ample distance between the light source and the refractometer proper. Because of the operating principle of the refractometer, the distance allowed for this purpose is limited. It has heretofore been generally held that if the light source is separated from the refractometer proper by a distance great enough for said temperatures to remain unaffected by the light source, then the refractometer is prevented from functioning to its full capacity.

The inventors have overcome this dilemma by giving a thermally insulated structure to one end portion of the refractometer and attaching the light source to the outside of said thermally insulated structure so that most of the heat generated by the lamp is dispersed into the ambient air and the light necessary for refractometry is projected into the interior of the refractometer. As illustrated in the drawings, the light source 21 is fixed on the outside of the outer shell 8 of thermally insulated structure. When the light source is formed as described above, the major part of the heat generated thereby is radiated through its socket into the atmosphere and a minor part thereof is conducted to the outer face of the outer shell 8, while no part of the heat reaches the central portion 12. The light emitted from the light source enters the central portion 12 in an amount large enough for passage through the array of lenses 9 to permit refractometry as required. To facilitate the radiation of heat through the socket of the light source 21, the illustrated embodiment incorporates a radiation fin.

The precision of the refractometer can be heightened by making the outer shell with a heat-insulating material and further forming the interior in a heat-insulating structure. In the illustrated embodiments, the optical base 13 is underlain by heat-insulating materials 10 and 11. In addition, an air layer 9 is formed inside the side walls and the top side. The air layer may be filled up with an insulating material to heighten further the heat insulating property. In this construction, the heat from the lamp in the light source as well as the heat outside the housing hardly reaches the central portion 12, whereas the light necessary for refractometry is admitted into the interior of the housing.

The central portion 12 must be maintained at a constant temperature. Maintenance of such a constant temperature is effectively accomplished by allowing a substance of large heat capacity to be held inside and causing the whole thermal energy delivered from the light source, the ambient air, the solvent and the test specimen to the central portion 12 to undergo exchange of heat so that the temperature is uniformly maintained throughout the enire space of the central portion 12.

To be specific, the optical base 13 made of a metal of large thickness occupies a large percentage of the space of the central portion 12. Therefore, the fact that this optical base 13 is made of a metal of large heat capacity constitutes one highly effective means for the maintenance of said constant temperature.

What is important is that the central portion 12 should be of a structure such as to eliminate any local temperature difference immediately. Otherwise, the central portion may be maintained, by heating, at a fixed temperature higher than the temperature outside the housing.

In the embodiment illustrated in FIGS. 3 and 4, the cell 16 is fastened to the optical base 13 through the medium of the cell supporting base 22. This intervention of the cell supporting base 22 is intended to retard the effect otherwise exerted upon the cell 16 even by the slightest change of temperature.

If in this case, the optical base is made of aluminum and the cell supporting base is made of stainless steel, then the cell is affected very little by the change in temperature of the optical base because the coefficient of heat conductivity of stainless steel is about 1/40 of that of aluminum.

The cell supporting base 22 may otherwise be made of a non-metallic substance which abounds in rigidity and durability. The cell supporting base 22 may be made of a good heat conductor when the temperature of the central portion 12 is positively controlled as by circulating hot water to the central portion, for example.

In the refractometer of the present invention, the cell, conduits, liquid chromatographic column, optical components and photoelectric sensor which have heretofore been used in the conventional refractometers may be used in their unmodified form. The groove 15 formed in the optical base to hold the chromatographic column and the column 18 may be held in tight contact with each other. Heat transfer between the optical base and the column may be improved by forming the groove with a cross section larger than the diameter of the column and filling the space with a flexible good heat conductor 23 as a heat-transfer medium. Copper wool is a typical example of a good heat conductor. The good heat conductor which is thus used to fill the space serves an additional purpose of obstructing free movement of air within the space and consequently precluding otherwise possible thermal disturbance due to air movement.

The lead-in tube for introducing the test specimen of liquid substance will be described.

The component separated by the chromatographic column must be introduced into the sensor cell without undergoing the phenomenon of remingling due to dispersion. To ensure freedom from such a danger, the inner volume of the lead-in tube must be decreased as much as possible. Generally, it is considered appropriate to fix the upper limit at 30 μl.

The lead-in tube for the test specimen, therefore, is desired to have a very small inner volume and possess a property such that the temperature of the test specimen in transit through the tube quickly approaches the temperature of the interior of refractometer and yet the temperature is distributed uniformly throughout the entire interior of tube.

Figure 5:
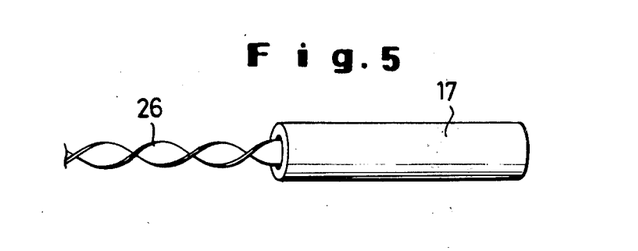
FIG. 5 is a perspective view illustrating a twisted thin plate inserted as the twisted member inside a conduit.
Figure 6:
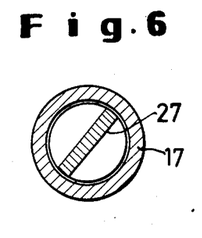
FIG. 6 is a cross-sectional view illustrating a twisted thin plate inserted as the twisted member inside a conduit.
Figure 7:
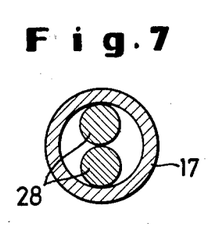
FIG. 7 is a cross-sectional view illustrating two metallic bars inserted as the twisted member inside a conduit.

To fulfil the requirement, the present invention purposes insertion of a twisted member inside the lead-in tube. The shape and size of this twisted member are required to be such that the liquid delivered through the tube is caused to flow in a spiral course. Examples of twisted members which are desirable for this purpose include two metallic wires spirally twisted around each other and twisted bars and plates. FIG. 5 illustrates a twisted thin plate 26 inserted as the twisted member in the lead-in tube 17. FIG. 6 illustrates a twisted thick plate 27 inserted similarly in the lead-in tube. FIG. 7 illustrates two twisted metallic wires 28 inserted similarly in the lead-in tube.

Figure 8:
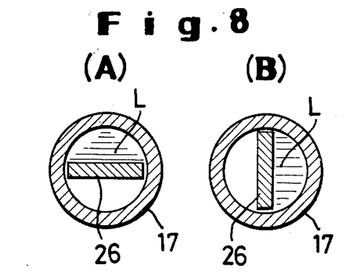
FIG. 8 is an explanatory diagram illustrating the movement of a liquid inside the conduit of FIG. 6.

The twisted member may be simply inserted within the lead-in tube 17. If the inserted twisted member has the possibility of enjoying some freedom of movement within the tube interior, then it may be deprived of the freedom of movement as by having the ends thereof soldered to the tube. The twisted members 26, 27 and 28 are held in intimate contact with the inner wall surface of the lead-in tube 17. Therefore when they are made of a material having a high heat conducting property, they will serve to enhance the efficiency of heat exchange. As the twisted member causes the liquid test specimen in transit through the tube to flow in a spiral course, the liquid is subject to the force exerted in the directions perpendicular to the axis of tube so that the portion of the liquid near the core of tube and the portion of the liquid close to the periphery are intermingled without entailing the phenomenon of turbulence, with the result that the heat-exchange efficiency is improved and the temperature distribution uniformized. FIG. 8(A) and FIG. 8(B) are explanatory diagrams illustrating the forces exerted by the twisted member 26 upon the liquid in transit. The liquid L which occupies the upper half portion of the circular cross section of FIG. 8(A) gradually changes its position as it advances along the spirally twisted surface of the twisted member 26. Then this liquid comes to assume the position indicated in FIG. 8(B). This means that the portions of the liquid which are in the opposite corners of FIG. 8(A) are drawn toward the center and the portion of the liquid which is at the center is moved partly to the top and partly to the bottom. Consequently, the portions of the liquid change position without entailing the phenomenon of turbulence which has adverse effects on the test specimen and the temperature of the liquid is uniformized.

The insertion of the twisted member in the lead-in tube, accordingly, brings about the advantage that the available surface area for exchange of heat is increased, the portion of the liquid which collides into the surface for heat transfer immediately changes position with other portion of the liquid and the temperature is uniformized. Since the insertion of the twisted member substantially decreases the inner volume of the lead-in tube, there is an additional advantage that a tube of a relatively large diameter can be used as the lead-in tube.

When the liquid chromatographic column is incorporated inside the housing, the lead-in tube for the test specimen may be laid inside the housing so as to establish a connection between the cell and the column. To permit analysis of varying samples, it is advantageous to give the refractometer a construction such that the liquid chromatographic column is not incorporated within the housing and the lead-in tube alone is set in a removable case and inserted in the housing.

Figure 9:
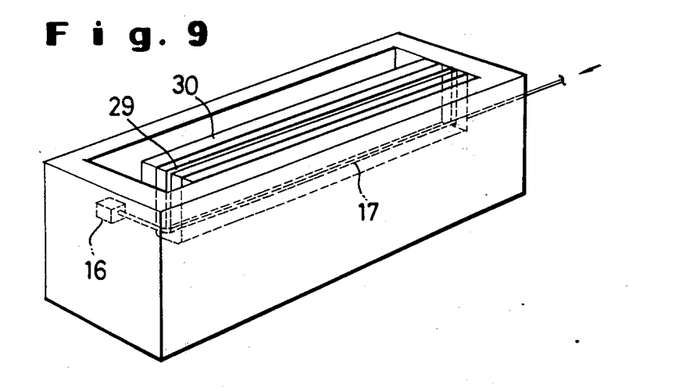
FIG. 9 is a model diagram illustrating a construction wherein the conduit is set in position inside a case and attached to a block of the refractometer.
Figure 10:
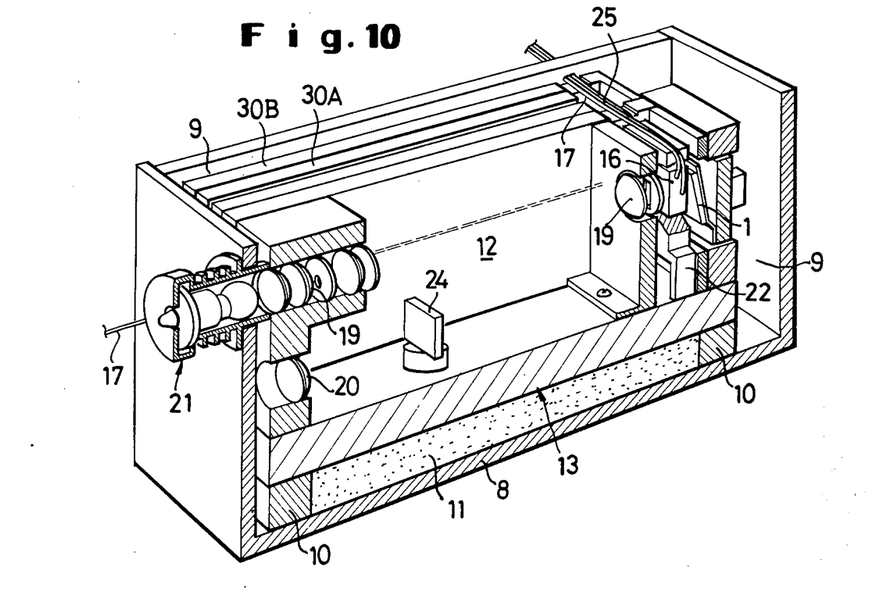
FIG. 10 is a perspective view of one embodiment wherein a conduit is set in position in a case and attached to the block of the refractometer.
Figure 11:
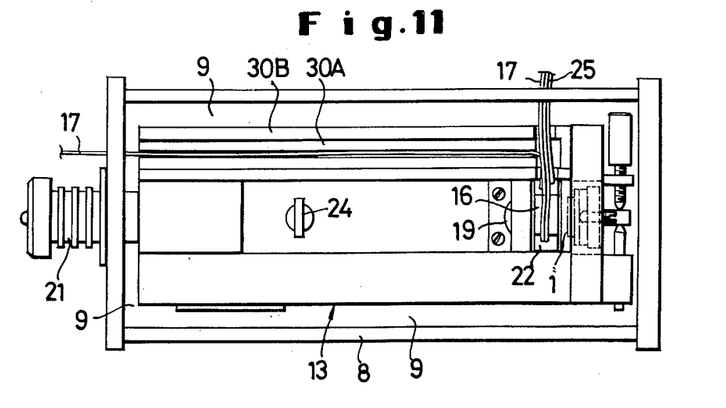
FIG. 11 is a plan view of the embodiment of FIG. 10.

FIG. 9 is a model diagram illustrating a construction wherein the case containing the lead-in tube is attached to the block of the refractometer. FIGS. 10 and 11 illustrate the construction of refractometer corresponding to that of FIGS. 3 and 4, except that the liquid chromatographic column is removed and a block incorporating said case containing the lead-in tube is attached instead.

FIG. 9 illustrates a construction wherein the lead-in tube 17 is coated with a heat-conducting paste and set in position at the bottom of a U-groove case 29 and the case 29 containing the lead-in tube is stowed into the metallic block 30 of the sensor. (In this drawing, the other parts are not indicated to show the interior structure of the block.)

One end of the lead-in tube 17 protrudes from the sensor and extends for connection with the column (not illustrated) and the other end thereof leads into the cell 16 inside the refractometer.

In the construction of FIGS. 10 and 11, the metallic block is divided into a block 30A serving to hold in position the U-groove case for containing the lead-in tube and a block 30B serving to receive the block 30A.

The refractometer of the construction illustrated in FIGS. 10 and 11 was tested, with the twisted member inserted in the lead-in tube and without use of said twisted member.

| Refractometer | |
|---|---|
| Cell capacity | 8 μl |
| Length of lead-in tube | 200 mm (stainless steel tube) |
| Diameter of lead-in tube | 1.6 mm (outside), 0.5 mm (inside) |
| Dimensions of twisted member | Two wires 0.2 mm in diameter twisted at a fixed pitch of 0.45 |
| Solvent | Pure water |
| Liquid subjected to measurement | Pure water |

Figure 12:
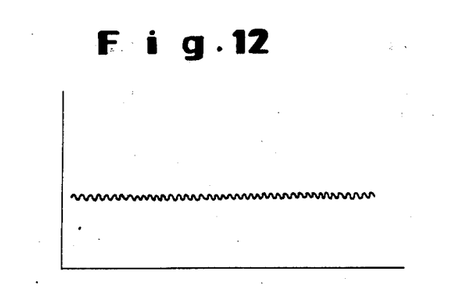
FIG. 12 is a graph showing a typical time-course change of the refractive index of a test specimen as measured by use of a refractometer having a twisted member inserted in the conduit.
Figure 13:
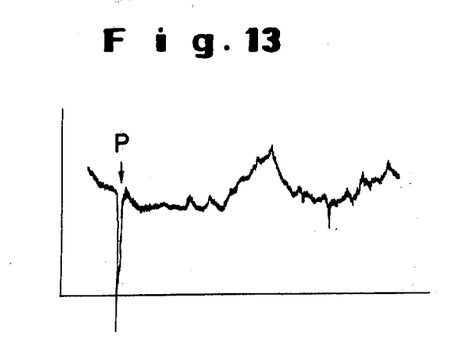
FIG. 13 is a graph showing a typical time-course change of the refractive index of a test specimen as measured under the same conditions as those of FIG. 12, except for omission of the insertion of the twisted member.

The results are graphically indicated in FIGS. 12 and 13. In the graphs, the horizontal axis is graduated for time of measurement (in minutes) and the vertical axis for index of refraction.

In the graph of FIG. 13, a sharp dip is shown at the position P. The point P represents the time when a human hand touched the tube for forwarding the liquid. This offers clear proof that the temperature of the liquid has an immense effect upon the value of refractive index registered by the sensor. A review of the graphs clearly shows that the curve of FIG. 12 representing the results involving the insertion of the twisted member in the lead-in tube is decisively stable as compared with the curve of FIG. 13 representing the results omitting the insertion.

The twisted member and the lead-in tube are desired to satisfy the following conditions:

| | |
|---|---|
| Inside diameter of lead-in tube | 0.2 mm to 1.0 mm |
| Inner volume of lead-in tube | 25 μl to 43 μl |
| Material of twisted member to be inserted | |
| Twisted member (plate), thickness | 0.05 mm to 0.2 mm |
| width | 0.2 mm to 0.9 mm |
| pitch | 0.4 to 1.5 |
| Twisted member (wire), diameter | 0.05 mm to 0.4 mm |
| pitch | 0.2 to 0.9 |
| Twisted member (bar), diameter | 0.2 mm to 0.8 mm |
| pitch | 0.7 to 1.5 |

When the refractometer of the foregoing description is put to actual use, the bearing of the reflecting mirror must be adjusted so that the light emitted from the light source, passed through the cell and reflected by the reflecting mirror will impinge upon the sensor at the predetermined position. The present invention further embrace means which permits this adjustment of the bearing of the reflecting mirror in the refractometer to be accomplished accurately and quickly.

A preferred embodiment of this invention in this respect will be described with reference to FIGS. 14, 15 and 16.

Figure 14:
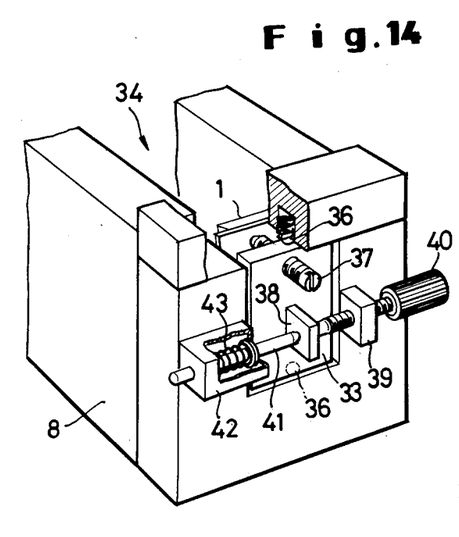
FIG. 14 is a perspective view of the reflecting mirror and the neighboring structure adapted to provide required adjustment of the optical axis according to the present invention.
Figure 15:
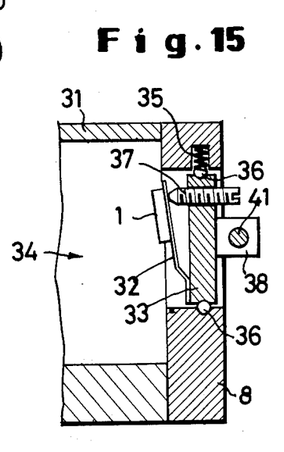
FIG. 15 is a cross section of the structure of FIG. 14.
Figure 16:
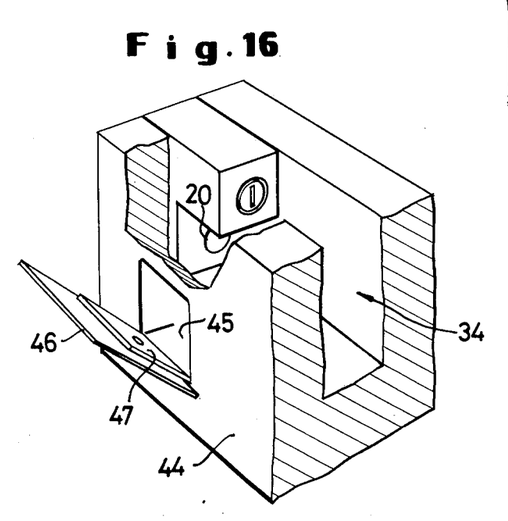
FIG. 16 is a perspective view of the portion including an inspection window providing a visual line directed to the reflected light detection unit.

FIGS. 14–16 are model explanatory diagrams illustrating the manners of attachment of the reflecting mirror. In FIG. 14 and FIG. 16, the top cover 31 is omitted for the convenience of illustration. By 1 is denoted a reflecting mirror which is fastened to a reflecting mirror supporting member 32. Denoted by 33 is a movable plate which is attached to the end of the housing of the refractometer. The movable plate is disposed substantially perpendicularly relative to the light path 34. The upper end of the plate is connected to the outer shell by the medium of a spring 35 and a steel ball 36 and the lower end of the plate is connected to the outer shell by the medium of a steel ball 36'. With this construction, the movable plate can freely be rotated about the axis which is formed through the two steel balls. The connection between the movable plate and the outer shell is not limited to the manner illustrated but may be established in any other manner on condition that it is permitted to rotate around said axis. The outer shell is formed on the inside of the housing of the refractometer. The lower end of the movable plate 33 is connected also with the reflecting mirror supporting base 32.

The movable plate 33 is pierced by a press member 37 which is disposed in a manner movable back and forth. In the illustrated embodiment, a threaded member is driven in a tapped hole formed in the movable plate. By rotating and moving this press member back or forth, therefore, the angle formed between the movale plate and the supporting base can be varied, with the joint of the movable plate and the supporting base as the axis of rotation. The construction so far described is one example. It may be in any other manner insofar as the supporting member and the movable plate are disposed in such a relationship that the angle formed therebetween is variable as described above.

Now, one specific example of the construction which permits the movable plate to be rotated around the vertical axis thereof will be described with reference to the drawings. By 38 is denoted a protruding plate which is attached protrudingly to the rear surface of the movable plate. Denoted by 39 is a member which is fixed to the outer frame and provided with a tapped hole. A knob member 40 is threaded so as to be screwed into said tapped hole and is provided with a knurl.

A spring shoe 42 which is fastened to the outer frame contains a push spring 42 held around a push rod 41. By the resilient force of the spring, the push rod 41 pushes the protruding plate 38. By rotating the knurled knob and moving the knob member 40 in or out, therefore, the protruding plate can be moved toward or off the spring shoe. As the protruding plate is pushed, the movable plate 33 is rotated around the vertical axis, causing the reflecting mirror to be moved simultaneously. The reflecting mirror, therefore, can change its bearing in both vertical and horizontal directions.

If the reflecting mirror supporting base 32 is made of a leaf spring, then the reflecting mirror can be moved simultaneously with the push screw 17.

In the construction of FIG. 16, an inspection window 45 is bored through the shell enclosing the light path 34 at a position close to the reflected light detection unit (photoelectric sensor) 20. A lid 46 having a mirror 47 attached to the inner face thereof is placed to close said inspection window. When this lid is opened as illustrated, the sensor 20 within the shell can be inspected with the aid of the mirror.

Required adjustment of the optical axis of the optical system in the refractometer is accomplished by opening the lid 46 aslant as illustrated in FIG. 16 so that the sensor 20 is reflected by the mirror 47 to be inspected from above and then changing the bearing of the reflecting mirror 1 until the light reflected by the reflecting mirror impinges upon the sensor at the prescribed position.

With the construction described above, the adjustment of the optical axis can be made very easily and quickly as compared with the conventional construction.

In the conventional refractometer, the upper lid must be removed each time the adjustment of the optical axis is made. The removal of the upper lid causes a change in the inner temperature of the refractometer and consequently affects the precision of the refractometer. This disadvantage has been eliminated by the incorporation of said inspection window and mirror.

What is claimed is:

1. A high-sensitivity differential refractometer, which comprises:
   a housing;
   a light source disposed outside the housing;
   light-refracting means disposed inside the housing and comprising a cell, lenses and a reflecting window provided with an optical axis adjusting unit attached to one end portion of the housing and comprising a reflecting mirror, a reflecting mirror supporting base and a movable plate; said reflecting mirror being fastened to said reflecting mirror supporting base, said reflecting mirror supporting base being attached at one end portion thereof to said movable plate, said movable plate being disposed substantially perpendicularly relative to the path of light from the light source and being provided with means for enabling the movable plate to be rotated around the vertical axis thereof, said reflecting mirror supporting base being provided with means for enabling the reflecting mirror supporting base to be rotated around said one end portion thereof attached to the movable plate so as to vary the angle formed thereby with reference to the movable plate, the lateral side of said housing containing an inspection window for permitting inspection of said reflecting mirror from outside the housing;
   light-sensing means disposed inside the housing;

an optical base disposed inside the housing;

a liquid chromatographic column disposed inside the housing; and a conduit for introducing the test specimen of liquid substance into the cell.

2. A high-sensitivity differential refractometer, which comprises:

a housing;

a light source disposed outside the housing;

light-refracting means disposed inside the housing and comprising a cell, lenses and a reflecting window provided with an optical axis adjusting unit;

light-sensing means disposed inside the housing;

an optical base disposed inside the housing;

a liquid chromatographic column disposed inside the housing; and a conduit adapted to introduce the test specimen of liquid substance into the cell and having a twisted member therein.

3. The high-sensitivity differential refractometer according to claim 2, wherein said optical axis adjusting unit is attached to one end portion of the housing and comprises a reflecting mirror, a reflecting mirror supporting base and a movable plate, said reflecting mirror is fastened to said reflecting mirror supporting base, said reflecting mirror supporting base is attached at one end portion thereof to said movable plate, said movable plate is disposed substantially perpendicularly relative to the path of light from the light source and is provided with means for enabling the movable plate to be rotated around the vertical axis thereof, said reflecting mirror supporting base is provided with means for enabling the reflecting mirror supporting base to be rotated around said one end portion thereof attached to the movable plate so as to vary the angle formed thereby with reference to the movable plate, and the lateral side of said housing contains an inspection window for permitting inspection of said reflecting mirror from outside the housing.

4. A high-sensitivity differential refractometer, which comprises:

a housing;

a light source disposed outside the housing;

light-refracting means disposed inside the housing and comprising a cell, lenses and a reflecting window provided with an optical axis adjusting unit;

light-sensing means disposed inside the housing;

an optical base disposed inside the housing;

a liquid chromatographic column disposed outside the housing; and a conduit adapted to introduce the test specimen of liquid substance into the cell, set in position in a case, contained in a removable state within a metallic block in the interior of the housing and having a twisted member therein.

5. A high-sensitivity differential refractometer, which comprises:

a housing;

a light source disposed outside the housing;

light-refracting means disposed inside the housing and comprising a cell, lenses and a reflecting window provided with an optical axis adjusting unit attached to one end portion of the housing and comprising a reflecting mirror, a reflecting mirror supporting base and a movable plate; said reflecting mirror being fastened to said reflecting mirror supporting base, said reflecting mirror supporting base being attached at one end portion thereof to said movable plate, said movable plate being disposed substantially perpendicularly relative to the path of light from the light source and being provided with means for enabling the movable plate to be rotated around the vertical axis thereof, said reflecting mirror supporting base being provided with means for enabling the reflecting mirror supporting base to be rotated around said one end portion thereof attached to the movable plate so as to vary the angle formed thereby with reference to the movable plate, the lateral side of said housing containing an inspection window for permitting inspection of said reflecting mirror from outside the housing;

light-sensing means disposed inside the housing;

an optical base disposed inside the housing;

a liquid chromatographic column disposed outside the housing; and a conduit adapted to introduce the test specimen of liquid substance into the cell, set in position in a case and contained in a removable state within a metallic block in the interior of the housing.

6. A high-sensitivity differential refractometer, which comprises:

a housing;

a light source disposed outside the housing;

light-refracting means disposed inside the housing and comprising a cell, lenses and a reflecting window provided with an optical axis adjusting unit attached to one end portion of the housing and comprising a reflecting mirror, a reflecting mirror supporting base and a movable plate; said reflecting mirror being fastened to said reflecting mirror supporting base, said reflecting mirror supporting base being attached at one end portion thereof to said movable plate, said movable plate being disposed substantially perpendicularly relative to the path of light from the light source and being provided with means for enabling the movable plate to be rotated around the vertical axis thereof, said reflecting mirror supporting base being provided with means for enabling the reflecting mirror supporting base to be rotated around said one end portion thereof attached to the movable plate so as to vary the angle formed thereby with reference to the movable plate, the lateral side of said housing containing an inspection window for permitting inspection of said reflecting mirror from outside the housing;

light-sensing means disposed inside the housing;

an optical base disposed inside the housing;

a liquid chromatographic column disposed outside the housing; and a conduit adapted to introduce the test specimen of liquid substance into the cell, set in position in a case, contained in a removable state within a metallic block in the interior of the housing and having a twisted member therein.

* * * * *